US008875712B2

(12) United States Patent
Koeller

(10) Patent No.: US 8,875,712 B2
(45) Date of Patent: Nov. 4, 2014

(54) SYSTEM AND METHOD FOR OCCLUDING A REPRODUCTIVE BODY LUMEN

(75) Inventor: Gregory L. Koeller, Apple Valley, MN (US)

(73) Assignee: Bayer Essure Inc., Milpitas, CA (US)

( * ) Notice: Subject to any disclaimer, the term of this patent is extended or adjusted under 35 U.S.C. 154(b) by 0 days.

(21) Appl. No.: 13/468,958

(22) Filed: May 10, 2012

(65) Prior Publication Data

US 2012/0221039 A1     Aug. 30, 2012

Related U.S. Application Data

(63) Continuation of application No. 12/556,262, filed on Sep. 9, 2009, now Pat. No. 8,322,341.

(60) Provisional application No. 61/095,340, filed on Sep. 9, 2008.

(51) Int. Cl.
*A61F 6/22*     (2006.01)
*A61F 6/24*     (2006.01)

(52) U.S. Cl.
CPC . *A61F 6/225* (2013.01); *A61F 6/22* (2013.01); *A61F 6/24* (2013.01)
USPC ............ 128/831; 128/830; 128/843; 606/135

(58) Field of Classification Search
CPC ....... A61F 6/20; A61F 6/22; A61B 17/12022; A61B 17/12163
USPC ......... 128/830–833, 839–843, 847, 887, 838; 623/1.11, 1.18, 1.2; 606/135–137, 153, 606/193
See application file for complete search history.

(56) References Cited

U.S. PATENT DOCUMENTS

| 5,935,137 | A | 8/1999 | Saadat et al. |
| 6,096,052 | A | 8/2000 | Callister et al. |
| 6,432,116 | B1 | 8/2002 | Callister et al. |
| 7,073,504 | B2 | 7/2006 | Callister et al. |
| 2001/0041900 | A1 | 11/2001 | Callister et al. |
| 2005/0045183 | A1 | 3/2005 | Callister et al. |
| 2005/0085844 | A1 | 4/2005 | Tremulis et al. |
| 2005/0192616 | A1 | 9/2005 | Callister et al. |

(Continued)

FOREIGN PATENT DOCUMENTS

| WO | WO/2007/133222 | 11/2007 |
| WO | WO/2009/017680 | 2/2009 |
| WO | WO/2009/075800 | 6/2009 |

*Primary Examiner* — Patricia Bianco
*Assistant Examiner* — Kari Petrik
(74) *Attorney, Agent, or Firm* — Blakely, Sokoloff, Taylor & Zafman LLP

(57) ABSTRACT

An occluding system is provided that can include a first occluding device (e.g., secondary occluder) and a second occluding device (e.g., primary occluder). Providing two devices can better promote effective occlusion within the body lumen and facilitate advantageous occlusion stages, such as initial and long-term occlusion stages. In various embodiments, the two occluding devices are in operative communication with one another, such that the second occluding device is adapted to couple with or slide along a tail portion of the first occluding device.

17 Claims, 11 Drawing Sheets

(56) References Cited

U.S. PATENT DOCUMENTS

| | | |
|---|---|---|
| 2005/0209633 A1 | 9/2005 | Callister et al. |
| 2006/0009798 A1* | 1/2006 | Callister et al. ............... 606/200 |
| 2007/0163601 A1* | 7/2007 | Pollock et al. ................ 128/843 |
| 2007/0261699 A1 | 11/2007 | Callister et al. |
| 2008/0135053 A1 | 6/2008 | Gruber et al. |
| 2008/0135054 A1 | 6/2008 | Callister et al. |
| 2008/0308110 A1 | 12/2008 | Callister et al. |
| 2009/0178682 A1 | 7/2009 | Tal et al. |
| 2009/0266366 A1* | 10/2009 | Swann et al. ................. 128/831 |
| 2010/0082056 A1* | 4/2010 | Mavani et al. ................ 606/192 |
| 2012/0318276 A1* | 12/2012 | Wildemeersch ............. 128/833 |

* cited by examiner

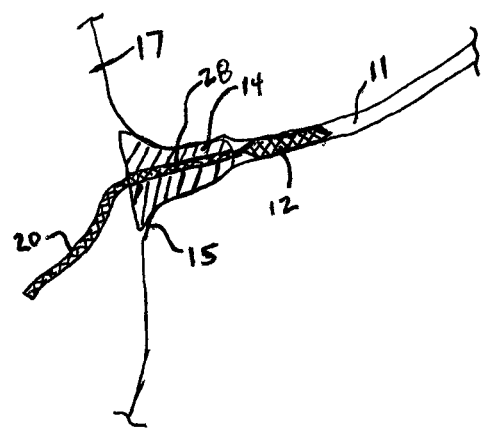
Fig. 14
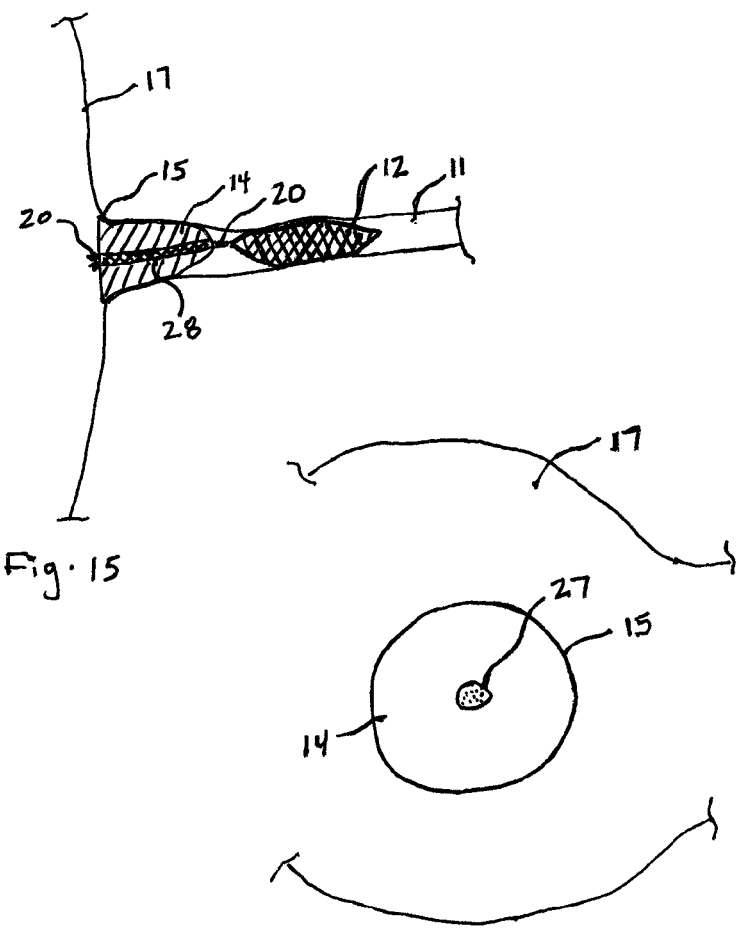
Fig. 15
Fig. 16

US 8,875,712 B2

SYSTEM AND METHOD FOR OCCLUDING A REPRODUCTIVE BODY LUMEN

RELATED APPLICATIONS

This application is a continuation of U.S. patent application Ser. No. 12/556,262 filed Sep. 9, 2009 now U.S. Pat. No. 8,322,341, and claims priority to and the benefit of U.S. Provisional Application No. 61/095,340, filed Sep. 9, 2008, which is incorporated herein by reference in its entirety.

FIELD OF THE INVENTION

The present invention relates generally to the field of occluding devices, delivery systems for such devices and the method of using such devices and systems in the occlusion of body lumens or passageways. The invention is particularly useful for the occluding reproductive lumens such as a female patient's fallopian tubes or a male patient's vas deferens to affect contraception.

BACKGROUND OF THE INVENTION

One form of contraception involves the occlusion of reproductive tracts, particularly, the fallopian tubes in female subjects and the vas deferens in male subjects, with an embolic material and/or occluding device that acutely and/or chronically (following foreign body tissue reaction or epithelialization) blocks passage of sperm through the reproductive tract. Particular forms of occluding devices and systems and methods of inserting the occluding devices in the vas deferens or fallopian tubes are described in commonly owned U.S. Pat. Nos. 6,096,052 and 6,432,116 and in commonly assigned U.S Patent Application Publication Nos. 2001/0041900, 2005/0045183, 2005/0085844, 2005/0192616, 2005/0209633, and 2006/0009798, for example, certain features of which are embodied in the Ovion® permanent contraceptive system sold by the assignee of the present invention.

It would be desirable to provide contraceptive occlusion systems that provide improved delivery and deployment systems, implant structures, and the effectiveness of occlusion.

SUMMARY OF THE INVENTION

The present invention is directed to a contraceptive or occluding system for occluding a reproductive tract or lumen to prevent the passage of reproductive cells there through. The occluding system can include a first occluding device (e.g., secondary occluder) and a second occluding device (e.g., primary occluder). Providing two devices can better promote effective occlusion within the body lumen and facilitate advantageous occlusion stages, such as initial and long-term occlusion stages. In various embodiments, the two occluding devices are in operative communication with one another to facilitate insertion, deployment and effective occlusion within the body lumen to prevent the passage of reproductive cells, eggs or sperm cells.

A relatively quick initial primary occlusion occurs when the second occluding device is inserted into the ostium and a secondary long-term occlusion occurs with the insertion of the first occluding device within the fallopian tubes (e.g., via obstruction and tissue in-growth within the device). As such, the second device serves as a primary occluder and the first device serves as a secondary occluder. A third mechanism for occlusion and contraception is provided for those embodiments where a tail of the first occluding device is left to extend into the uterus as an intra-uterine device.

In various embodiments, the second occluding device can include a lumen there through adapted to receive and travel along a length of the tail of the first occluding device. Further, the second occluding device can include protruding members or textured portions to grab onto the tail, and the outer surface of the second occluding device can include protruding members or textured portions to facilitate fixation within or against the ostium tissue.

A catheter delivery system can be used to insert and position the first occluding device within the fallopian tubes of the patient. A needle delivery tool can be utilized to insert and position the second occluding device within the ostium of the patient. In other embodiments, a single delivery system can be employed to insert and deploy both the first and second occluding devices.

Various embodiments of the occluding device or member will include structures and materials to promote occlusion, such as denuding features, gels, frames, coatings, and the like.

Various contraceptive occlusion devices and delivery systems disclosed in U.S. Patent Application Publication Nos., 2005/0045183, 2005/0209633, 2006/0009798 and 2008/0308110, as well as PCT Patent Application Publication No. 2007/133222 can be employed, in whole or in part, with the present invention. As a result, each of the above-identified disclosures and publications is incorporated herein by reference in its entirety.

BRIEF DESCRIPTION OF THE DRAWINGS

FIG. 14 schematically shows the positioning of primary and secondary occluding devices, having an extending tail member, within a body lumen in accordance with embodiments of the present invention.

FIG. 15 schematically shows the positioning of primary and secondary occluding devices, having a trimmed tail member, within a body lumen in accordance with embodiments of the present invention.

FIG. 16 schematically shows a plug inserted within a lumen of an occluding device in accordance with embodiments of the present invention.

DETAILED DESCRIPTION OF PREFERRED EMBODIMENTS

Figure 1:
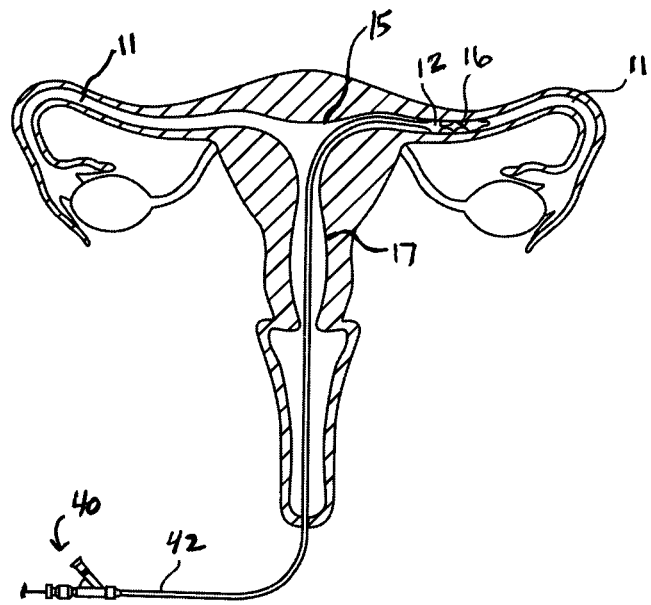
FIG. 1 schematically shows the delivery and insertion of an occluding device within a female's fallopian tube in accordance with embodiments of the present invention.

In the following detailed description, references are made to illustrative embodiments of methods and apparatus for carrying out the invention. It is understood that other embodiments can be utilized without departing from the scope of the invention. Preferred methods and apparatus are described for occlusion of reproductive body lumens to affect contraception.

It will be understood that the term "contraceptive device," "occlude," "occluding device," "implant," "occluding implant" or "occluding member" encompass any type of a device adapted to be delivered into and released or otherwise disposed in a reproductive tract or lumen to acutely and/or chronically occlude the reproductive tract lumen.

Referring generally to FIGS. 1-16, a contraceptive occluding system 10 is provided. The occluding system 10 can include a first occluding implant or device 12 (e.g., secondary occluder, distal occluding device) and a second occluding implant or device 14 (e.g., primary occluder, primary occluding device). Providing two devices can better promote effective occlusion within the body lumen and facilitate advantageous occlusion stages, such as initial and long-term occlusion stages. In various embodiments, the occluding devices 12, 14 are in operative communication with one another to facilitate insertion, deployment and effective occlusion within the body lumen to prevent the passage of reproductive cells, eggs or sperm cells.

In one embodiment, as shown in FIGS. 3-9, the first occluding device 12 can include a tubular member 16 having a first end 18, a second end 21, and a lumen extending there between. The tubular member 16 can be constructed and configured to support or promote tissue in-growth.

The tubular member 16 of the first occluding device 12 may be constructed of compatible mesh, Nitinol, length of shape-memory hypodermic tubing, shape-memory wire, slotted plastic or metal tubing, braided tubing or material, and can take on or resemble the shape of a ribbon, ring, coil, spring, and a myriad of other shapes and designs. Various exemplary configurations of the tubular member 16 are depicted in FIGS. 3-9. Further, the tubular member 16 can include bundled strands, woven strands, polymers, metals, protrusions or extending portions, treated animal tissues and like structures or designs to promote epithelialization and tissue in-growth. For instance, polyester or other polymer fibers may be attached to one or more expandable segments of the tubular member 16 to bear against the fallopian tube 11 wall such that tissue fixation and in-growth into the lumen occurs more rapidly. Additionally, the tubular member 16 may be surface coated or impregnated with epithelialization-promoting agents, drugs or other materials to enhance tissue impregnation.

A slow-release contraceptive substance may also be embedded with one or more of the devices 12, 14 to facilitate contraception during the time that it takes for tissue in-growth to occur, as disclosed in the above-referenced U.S. Patent Application Publication Nos. 2005/0045183 and 2006/000798, for example. The occluding devices 12, 14 may take other forms as shown in the various embodiments of occluding devices depicted in the incorporated patent references, or as otherwise known in the art.

Figure 17:
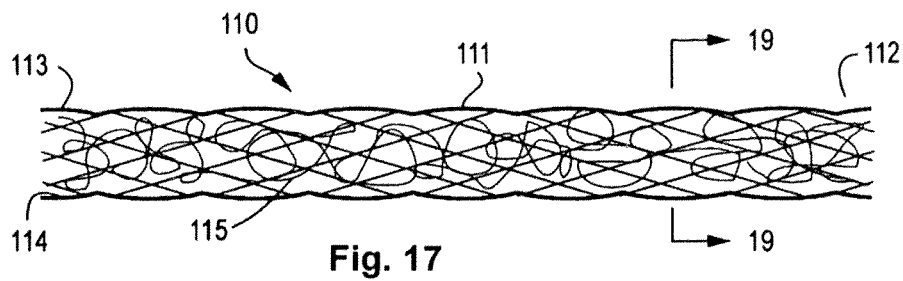
FIG. 17 is an elevational view of one embodiment of the occlusive device of the invention with the tubular member in a contracted configuration.

In one embodiment, either occluding device 12, 14 can be an occlusive device 110, as discussed in U.S. Patent Application Publication No. 2006/000798, embodying features of the present invention generally comprising a tubular member 111 having a first end 112, a second end 113, and a lumen 114 extending therein, as shown in FIG. 17.

Figure 18:
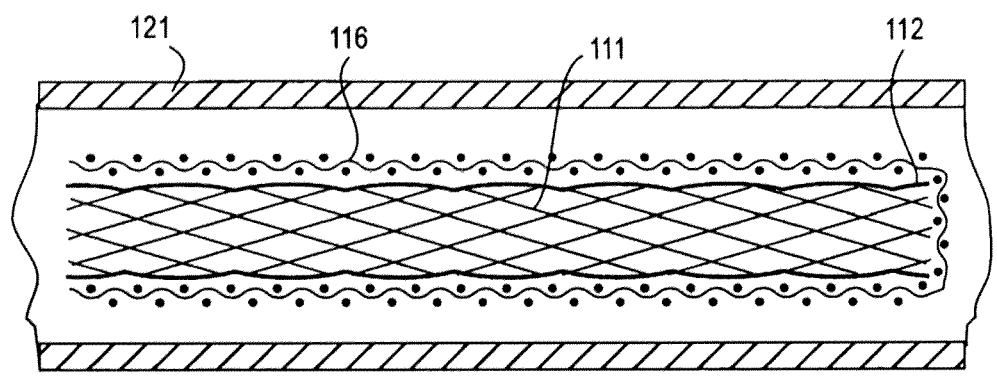
FIG. 18 is a side view partially in cross-section illustrating another embodiment of the occlusive device having a mesh layer on an outer surface of the tubular member, within a body lumen.

In another embodiment, as illustrated in FIG. 18 a mesh layer 116 is provided along at least a section of the outer surface and/or the inner surface of the tubular member 111, to facilitate tissue epithelialization along the tubular member 111 and into the mesh member 115. In the embodiment illustrated in FIG. 18, the mesh layer 116 is disposed along the entire length of the outer surface of the tubular member 111 and transversely disposed at the first end 112 of the tubular member 111. The mesh layer 116 may be an integral extension of the mesh member 115, or a separate member connected to or separate from the mesh member 115. In a presently preferred embodiment, the mesh layer 116 comprises woven or bundled strands of a, preferably, biocompatible material, which may be a single or a plurality of mesh sheets, as discussed above in connection with the mesh member 115. The mesh layer 116 is permeable to allow for tissue ingrowth, and consequently, facilitates ingrowth within the mesh member 115, as for example, in embodiments in which only a section of the tubular member 111 is expanded into contact with a wall of the body lumen 121, as discussed below. In this embodiment, the galvanic action may be created by using different metals for the exterior mesh of the tubular member 111, or by constructing the tubular member 111 of wire elements of at least two different metals.

Figure 19:
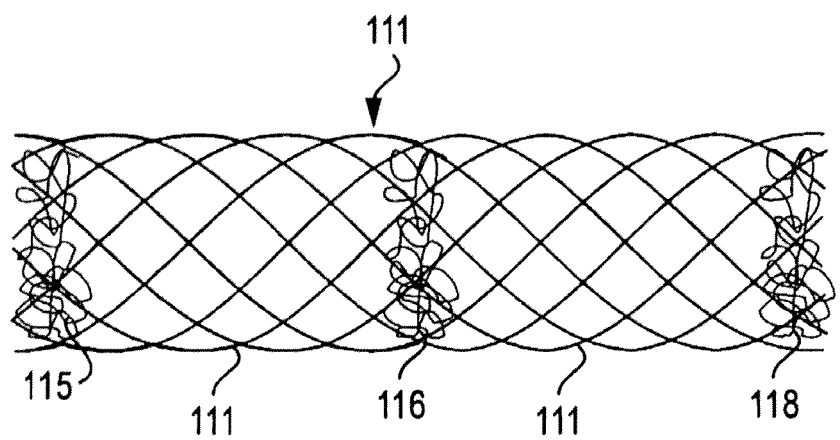
FIG. 19 is an elevational view of another embodiment of the occlusive device of the invention having a mesh member comprising bundled strands intermittently spaced in a plurality of sections of the tubular member.

The tubular member 111 may be expanded in the body lumen 121 using a balloon catheter, or alternatively, it may be self-expanding. The tubular member 111 is preferably self expanding in the embodiment in which the mesh member 115 is disposed along the length of the tubular member 111, as in the embodiment illustrated in FIG. 17, or is disposed at least in part at the second end 113 of the tubular member 111, as in the embodiment illustrated in FIG. 19.

Figure 20:
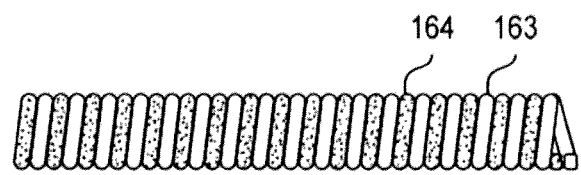
FIG. 20 is a side view of the occlusive device of the invention wherein the tubular element is comprised of two helical coils with their coils interlaced.
Figure 21:
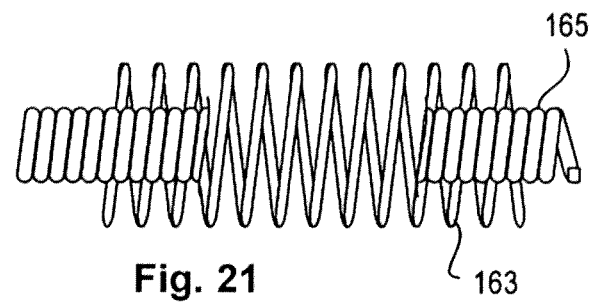
FIG. 21 is a side view of the occlusive device of the invention wherein the tubular element is comprised of two helical coils, one within the other.

In another embodiment, as shown in FIGS. 20 and 21 tubular member 111 is a coil 163 of wire or ribbon. It is obvious that a variety of other suitable configurations may be used for tubular member 111, such as a number of closed sinusoidal rings of wire or ribbon. In FIGS. 20 and 21, two coils 163, 164 and 165 made of metal different from each may form the galvanic effect. In FIG. 20, the coils 163 and 164 are interspersed with each other (one may be "screwed into" the other), or as in FIG. 21, one coil 165 may be contained within the other coil 163.

Figure 22:
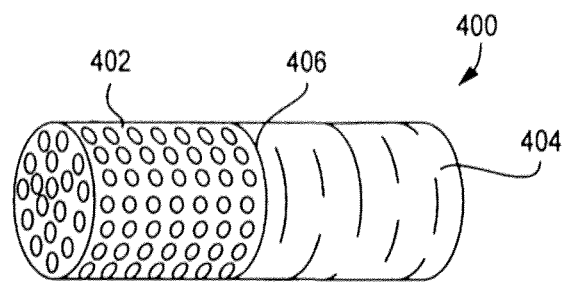
FIG. 22 is a side perspective view of one embodiment of the occlusive device of the present invention.
Figure 23:
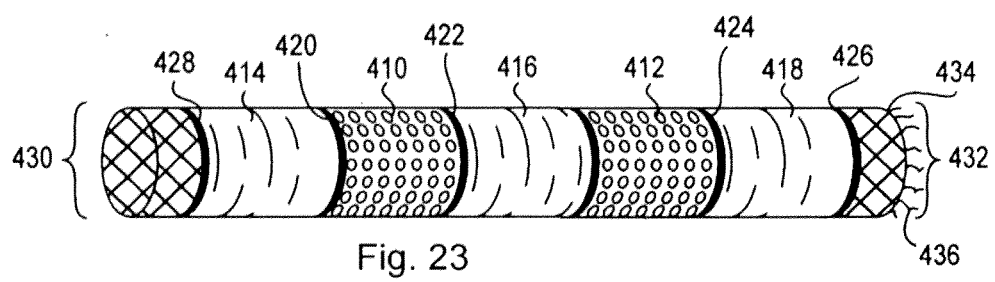
FIG. 23 is a side perspective of another embodiment of the occlusive device of the present invention.

Referring to FIGS. 22-23, in another embodiment, either occlusive device 12,14, is in the form of a foam plug 400. The plug may be comprised of segments. For example, a first segment 402 may be comprised of open celled foam and a second segment 404 may be comprised of solid material that is compressible or compressible closed cell foam. The segments 402, 404 are separated by a membrane 406, or formed in alternating sections.

The plug 400 may have various configurations. It may comprise multiple segments as show on in FIG. 23. The segments may alternate between permeable open cell segments 410, 412 that permit and may even enhance tissue ingrowth, and closed cell segments 414, 416, 418 and may be divided by membranes 420, 422, 424. There may also be membranes 426, 428 at the ends of the plug. There may in some embodiments be short stent-like portions 430, 432 at the ends of the plug 400 to anchor the plug 400 in place once it has been place and to resist expulsion by the body lumen, e.g. the cilia of the fallopian tube. The short stent-like portions 430, 432 may have projecting wires 434, 436 to firmly attach the plug 400 to the surface of the lumen wall.

Figure 24A:
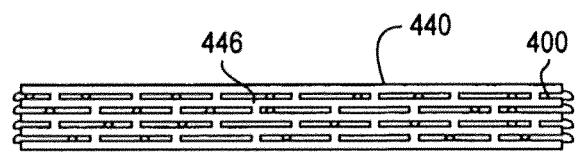
FIG. 24A is a side view of the occlusive device shown in FIGS. 22 and 23 encased in a stent-like structure.
Figure 24B:
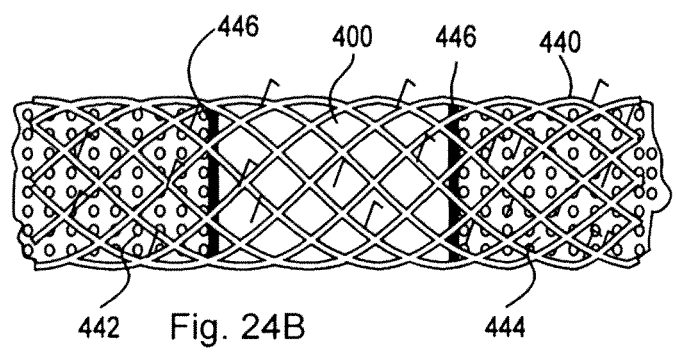
FIG. 24B is another embodiment of the occlusive device encased in a stent-like structure.

In an alternative embodiment, see FIGS. 24A and 24B, the foam plug 400 may be encased in a stent-like structure 440. The plug 400 could take any of the forms as discussed above, for example the plug 400 may contain permeable open cell segments 442, 444 separated by membranes 446 and be contained within the stent-like structure 440 either in place of or in addition to fibers that encourage tissue ingrowth. The stent-like structure 440 and the foam plug 400 are both shown in FIG. 24A in their unexpanded configuration, and they may expand to an expanded configuration as shown in FIG. 24B. The pressure of the foam plug 400 to expand may assist in expanding the stent-like structure 440 or the stent-like structure 440 may be self-expanding as described above. The plug 400 may be preformed and inserted into the stent-like structure 440, or may be formed in the stent-like structure 440, for example by injecting the plug 400 into a stent-like structure 440 and after the plug 400 has dried and formed, compressing the stent-like structure 440.

Figure 25:
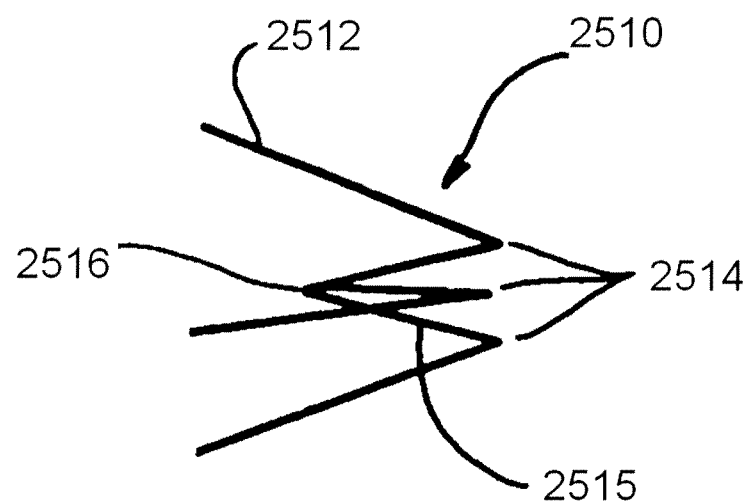
FIG. 25 is a side view of one embodiment of a lumen occluding and/or substance delivery device according to the present invention.

In another embodiment, either occluding device 12, 14 can be an occlusive device 2510, as discussed in U.S. Patent Application Publication No. 2005/0045183, having a plurality of first leg segments 2515 emanate from a central apex 2516, as shown in FIG. 25. Each first leg segment 2515 is joined at an angle with a second leg segment 2512, thereby forming a plurality of secondary apices 2514, as shown. When the device 2510 is expanded or allowed to expand within a body lumen, the second leg segments 2512 will contact and exert a constant outward force on the wall of the body lumen in which the device 2510 is positioned thereby maintaining in a substantially stationary position within that body lumen. Sometimes at least one of the second leg segments 2512 may be formed of thin, relatively rigid material and/or may comprise a projection (e.g., a hook, barb, etc.) that will lodge in the lumen wall to secure the device 2510 in place.

Figure 2:
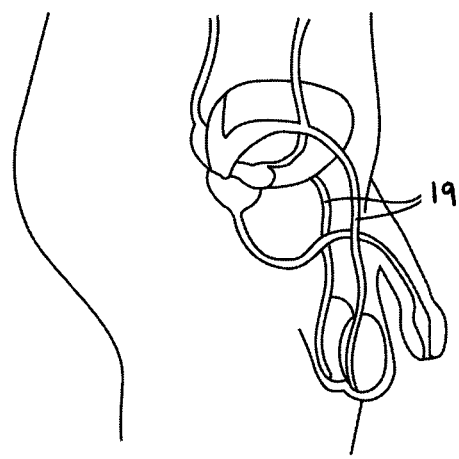
FIG. 2 schematically shows the relevant male anatomy, including the vas deferens.
Figure 3:
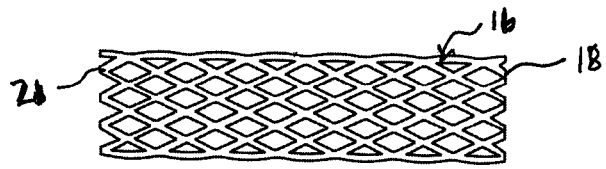
FIGS. 3-9 show exemplary tubular members of an occluding device in accordance with embodiments of the present invention.
Figure 4:
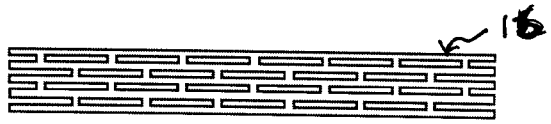
Figure 5:
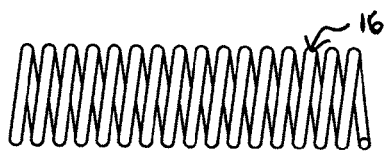
Figure 6:
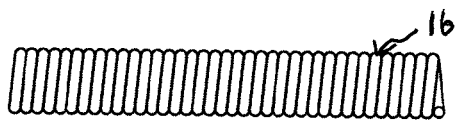
Figure 7:
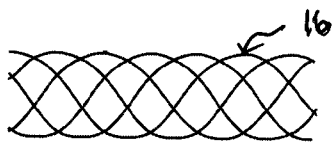
Figure 8:
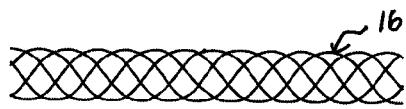
Figure 9:
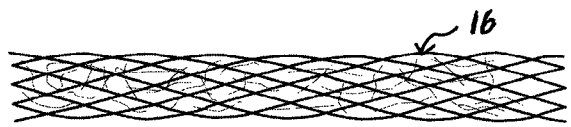
Figure 13:
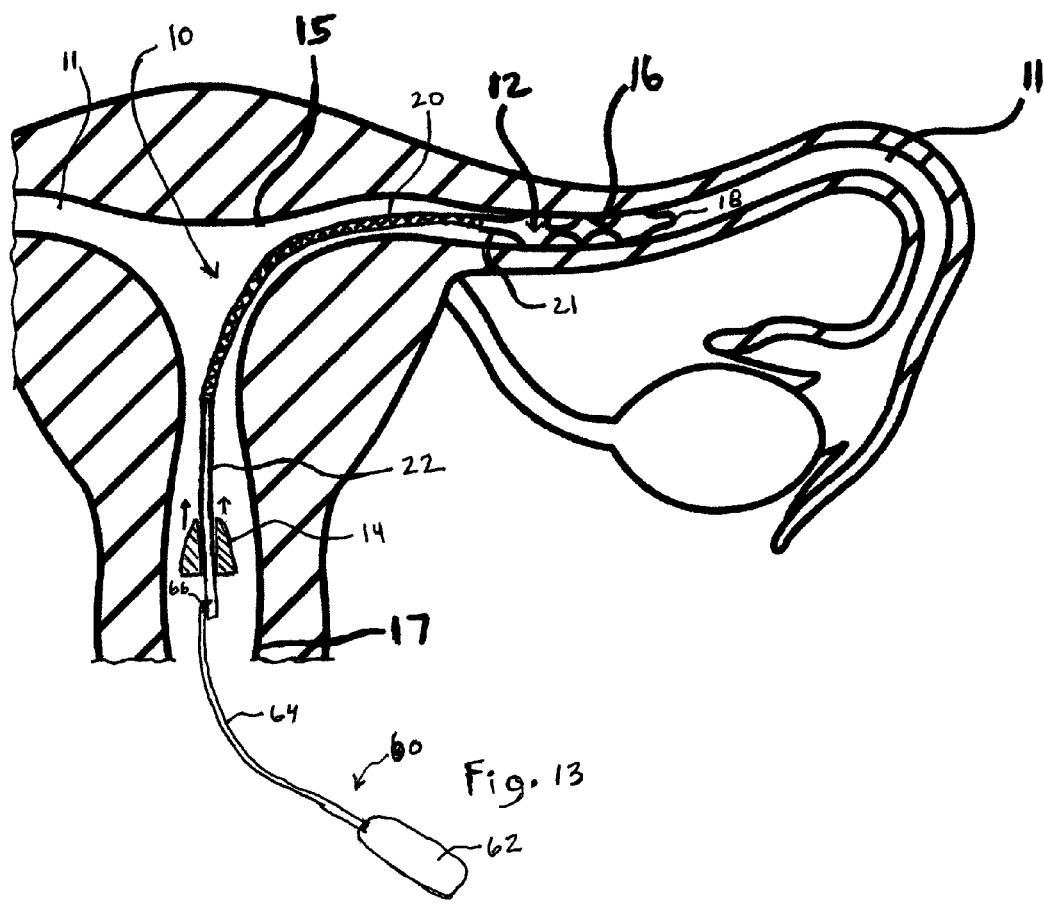
FIG. 13 schematically shows the delivery and insertion of primary and secondary occluding devices in accordance with embodiments of the present invention.

As shown in the embodiments of FIG. 13, the second occluding device 14 can be brought into operative communication with the first occluding device 14 such that both devices are capable of selective insertion and positioning within the body lumen, e.g., the female fallopian tubes 11 or the vas deferens 19 of a male patient (FIG. 2).

Such a configuration promotes and effects improved contraception. For example, as described further herein, the occluding device 12 can be first inserted into the body lumen, followed by insertion of the occluding device 14 to provide for secondary and primary occlusion, respectively. While the devices 12, 14 are described herein as having exemplary configurations, the dimensions, materials, shapes, and sizes can vary greatly to promote the desired occlusion of the body lumen. Further, the procedures and steps described herein can be employed bilaterally, e.g., to both fallopian tubes 11.

Referring generally to FIGS. 13-15, the first occluding device 12 can include a tail member or portion 20 extending from a portion of the first occluding device 12. The tail portion 20 can be a polymer material, such as a mesh strip, of a predetermined length. In one embodiment, the tail portion 20 can extend such that at least a length will trail out the ostium 15 and into the uterus 17. Further, the tail portion 20 can include a rod member 22 in certain embodiments. The rod member 22 can extend from the mesh tail portion 20 and can be shaped, sized and configured to receive or travel along at least a portion of the second occluding device 14. In various embodiments, the tail portion 20 can be constructed of known compatible materials, such as polymer mesh, non-mesh materials, solid members, and the like. The tail portion 20 and/or rod member 22 can be generally flexible, semi-rigid, or rigid, and can extend from any portion of the device 12.

Figure 10:
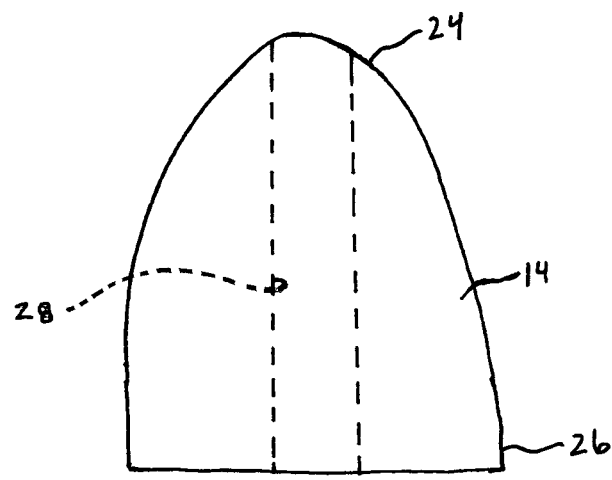
FIGS. 10-11 show exemplary occluding devices in accordance with embodiments of the present invention.
Figure 11:
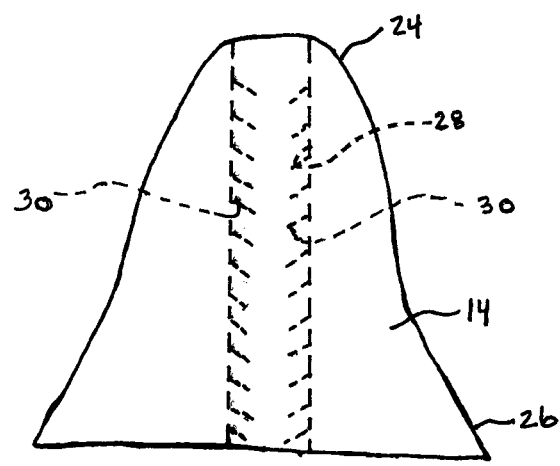

The second occluding device 14 can include a first end 24, a second end 26 and an inner lumen 28 extending from the first end 24 to the second end 26, as shown in FIGS. 10-11. In certain embodiments, the device 14 can be tapered such that the second end 26 is larger in cross-section than the first end 26. In other embodiments, the device 14 can take on a myriad of acceptable shapes and designs, including a bell-shape, tubular, flanged, lattice construction and like shapes or structures. Further, the occluding device 14 can be constructed of various polymer or other known compatible materials, including solid, mesh, non-mesh and like constructs.

In certain embodiments, the inner lumen 28 can include a plurality of extending protrusions or members 30 (e.g., angled teeth members, fibers, etc.) adapted to grab and retain sections of the tail portion 20 of the occluding device 12 during insertion and positioning of the devices. In other embodiments, the inner lumen 28 can include one or more textured portions adapted to facilitate gripping and retention of the tail portion 20. In addition, the outer surface of the device 14 can include one or more textured portions, protruding members, fibers, etc., to facilitate attachment of the device 14 against or within body tissue.

Figure 12:
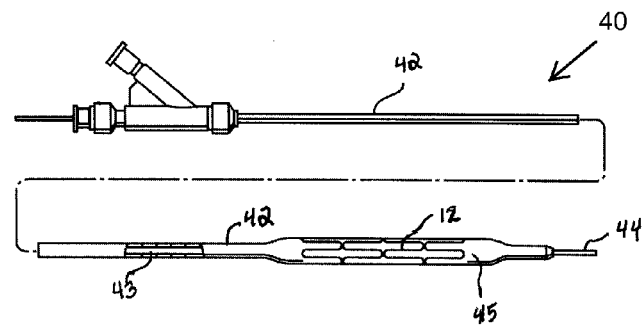
FIG. 12 shows an exemplary catheter delivery system for use in delivering an occluding device in accordance with embodiments of the present invention.

Referring generally to FIGS. 1 and 12, an embodiment of a catheter delivery system 40 is shown. The catheter system 40 can include an elongated shaft 42 having a lumen 43 which is in communication with a member 44 on a distal portion 45 of the catheter shaft 42. The occluding device (e.g., device 12) can be disposed at the distal shaft 42, within the lumen 43 of the shaft 42, or along the member 44 extending from the shaft 42. The occluding device 12 can be formed so that it has a collapsed configuration (e.g., with shape memory) with relatively small transverse dimensions. For example, the occluding device 12 may be deformed to facilitate mounting or disposal onto or within the shaft 42 and is expandable to an open expanded configuration within a body lumen when deployed from the catheter 40. Other known catheter delivery systems, and occluding systems and members, can be employed with the present invention, including those disclosed in U.S. Pat. No. 7,073,504, and U.S. Patent Publication Nos. 2005/0045183, 2005/0209633, 2007/0261699, 2008/0135054 and 2008/0308110, each of which is hereby incorporated by reference in its entirety.

Upon deployment to the body lumen (e.g., through the uterus, ostium and into the fallopian tube 11), the device 12 can be expanded to a larger dimension. The expansion of the diameter of occluding device 12 can be effected either by use of an expanding device, e.g., an inflatable balloon at the delivery catheter distal end that is disposed within the catheter lumen 44, or by self-expansion upon release from confinement within the delivery catheter. In an expanded configuration, the device 12, and tubular member 16 in particular, has an open, lattice-type structure facilitating epithelialization or tissue in-growth. Such tissue in-growth assists in securing the occluding device 12 to the tissue wall of the reproductive tract or body lumen. In one embodiment, the device 12 is expanded or self-expands to a diameter equal to or slightly larger than the inner diameter of the respective body lumen. For example, the expanded transverse dimension or diameter of the tubular member 16 can be approximately 0.1 mm to about 5 mm for disposition and retention within a female patient's fallopian tubes 11. The catheter 40 can be advanced under fluoroscopic or endoscopic visualization until occluding device 12 is positioned within one of the female patient's fallopian tubes 11.

FIGS. 13-16 show insertion and deployment techniques for the second occluding device 14. In one embodiment, a delivery tool 60 can be used to insert, direct and position the occluding device 14 within the uterus and into the uterine ostium 15, or the body lumen 11. The delivery tool 60 can include a handle portion 62, a needle portion 64, with the needle portion 64 including a distal end portion 66. The needle portion 64 can be straight, curved, helical, or can take on any other shape or configuration adapted to facilitate insertion, maneuvering around anatomical structures, and deployment of the device 14 within the patient. In certain embodiments, the needle portion 64 is curved to better assist in pushing the occluding device 14 into the ostium 15 without visually observing the implant. Embodiments of the delivery tool 60 can take on various know forms, and/or employ the delivery techniques as disclosed in PCT International Application Publication Nos. WO2009/075800 and WO2009/017680, which are incorporated by reference herein in their entirety.

The device 14 is adapted to travel or slide along the tail 20 (and/or rod member 22) such that the tail 20 passes through the lumen 30 of the device 14. Upon traversal of the device 14 along the tail 20 via the tool 60, the device 14 can be inserted into and positioned within the uterine ostium 15 of the patient. Upon deployment, at least a portion of the tail 20 is generally extending from the second end 26 of the device 14. At this point, the tail 20 can be cut off or otherwise removed proximate the device 14. Alternatively, the tail 20, or a portion thereof, can remain extending into the uterus 17 of the patient to provide further occlusion (e.g., act as an intra-uterine device). A compatible adhesive, gel or like material can be applied to the juncture between the extending tail 20 and the second end 26 of the lumen 30 to seal openings or gaps.

For those embodiments where the tail 20 is removed or cut off at or proximate the occluding device 14, various structures or techniques can be implemented to seal off the lumen 30 at the second end 26 of the device 14. For example, a plug 27 can be inserted into the second end 26 of the lumen 30 to close off the opening, as shown in FIG. 16. The plug 27 can also serve to push any remaining portion of the tail 20 into the lumen 30 (e.g., bunching the remaining tail 20 within the lumen 30). In certain other embodiments, a compatible adhesive, gel or like material can be inserted into the second end 26 of the lumen 30. Sealing or closing off of the lumen 30 can provide additional occlusion benefits.

The disclosed embodiments of the present invention utilize both occluding devices 12, 14 to provide a primary and secondary occlusion system and method. Namely, a relatively quick initial primary occlusion occurs when the occluding device 14 is inserted into the ostium 15 and a secondary long-term occlusion occurs with the insertion of the occluding device 12 within the fallopian tubes 11 (e.g., tissue in-growth within the device 12). As such, the device 14 serves as a primary occluder and the device 12 serves as a secondary occluder. A third mechanism for occlusion and contraception is provided for those embodiments where the tail 20 is left to extend into the uterus 17 as an intrauterine device.

All patents and publications referenced herein are hereby incorporated by reference in their entireties.

It will be understood that certain of the described structures, functions and operations of the above-described preferred embodiments are not necessary to practice the present invention and are included in the description simply for completeness of an exemplary embodiment or embodiments. It will also be understood that there may be other known structures, functions and operations ancillary to the typical surgical procedures that are not disclosed, but that can be implemented to practice the present invention. It is, therefore, to be understood that within the scope of the appended claims, the invention may be practiced other than as specifically described without actually departing from the spirit and scope of the present invention.

What is claimed is:

1. A system for occluding a body lumen comprising:
   only two occlusion devices, the two occlusion devices including a proximal occlusion device and a distal occlusion device, wherein the distal occlusion device comprises an expandable tubular member and an inner lumen within the expandable tubular member;
   a flexible and bunchable tail member that extends proximally from the distal occlusion device, and the proximal occlusion device is coupled to the tail member;
   wherein the distal occlusion device and the proximal occlusion device are coupled together only with the flexible and bunchable tail member extending between the distal occlusion device and the proximal occlusion device.

2. The system of claim 1, wherein the tail member comprises a polymer.

3. The system of claim 1, wherein the proximal occlusion device surrounds the tail member.

4. The system of claim 1, wherein the distal occlusion device is self-expandable.

5. The system of claim 4, wherein a cross-section of the inner lumen expands as the expandable tubular member self-expands from a contracted state to an expanded state.

6. The system of claim 1, wherein the distal occlusion device comprises an outer coil and an inner coil.

7. The system of claim 1, wherein the distal occlusion device comprises fibers within the tubular member.

8. The system of claim 1, wherein the proximal occlusion device is expandable.

9. The system of claim 8, wherein the proximal occlusion device is self-expandable.

10. The system of claim 9, wherein the proximal occlusion device is a plug.

11. The system of claim 10, wherein the plug comprises permeable open cell segments.

12. The system of claim 1, wherein both the proximal occlusion device and the distal occlusion device are self-expandable.

13. The system of claim 1, wherein the distal occlusion device comprises fibers to support tissue ingrowth for permanent occlusion of the body lumen, and the proximal occlusion device is a polymer plug that provides immediate occlusion of the body lumen.

14. A system for occluding a body lumen comprising:
   only two occlusion devices, the two occlusion devices including a proximal occlusion device and a distal occlusion device, wherein the distal occlusion device comprises a plurality of self-expanding leg segments emanating from a central apex;

a flexible and bunchable tail member that extends proximally from the distal occlusion device, and the proximal occlusion device is coupled to the tail member;

wherein the distal occlusion device and the proximal occlusion device are coupled together only with the flexible and bunchable tail member extending between the distal occlusion device and the proximal occlusion device.

15. The system of claim 14, wherein the distal occlusion device comprises fibers.

16. The system of claim 14, wherein the proximal occlusion device comprises a plug.

17. The system of claim 14, wherein the distal occlusion device is self-expandable.

* * * * *